(12) United States Patent
Tacha

(10) Patent No.: US 8,603,765 B2
(45) Date of Patent: Dec. 10, 2013

(54) IMMUNOASSAY REAGENTS AND METHODS OF USE THEREOF

(75) Inventor: David Tacha, Danville, CA (US)

(73) Assignee: Biocare Medical, LLC., Walnut Creek, CA (US)

( * ) Notice: Subject to any disclaimer, the term of this patent is extended or adjusted under 35 U.S.C. 154(b) by 11 days.

(21) Appl. No.: 12/606,309

(22) Filed: Oct. 27, 2009

(65) Prior Publication Data

US 2010/0047825 A1    Feb. 25, 2010

Related U.S. Application Data

(63) Continuation of application No. 10/784,163, filed on Feb. 24, 2004, now abandoned.

(51) Int. Cl.
| | | |
|---|---|---|
| G01N 33/53 | (2006.01) | |
| G01N 33/543 | (2006.01) | |
| G01N 33/554 | (2006.01) | |
| G01N 33/567 | (2006.01) | |
| G01N 33/574 | (2006.01) | |
| G01N 33/577 | (2006.01) | |
| C12Q 1/28 | (2006.01) | |
| C12Q 1/42 | (2006.01) | |
| C07K 16/18 | (2006.01) | |
| C12N 5/16 | (2006.01) | |

(52) U.S. Cl.
USPC ........... 435/7.9; 435/7.1; 435/7.21; 435/7.23; 435/7.24; 435/7.92; 435/7.95; 435/21; 435/28; 435/40.52; 435/960; 435/973; 436/501; 436/503; 436/519; 436/164; 436/813; 530/388.2; 530/389.1; 530/391.1; 530/391.3

(58) Field of Classification Search
USPC ............... 435/7.1, 7.21, 7.23, 7.24, 7.9, 7.92, 435/7.95, 21, 28, 40.52, 960, 973; 436/501, 436/503, 519, 164, 813; 530/388.2, 389.1, 530/391.1, 391.3
See application file for complete search history.

(56) References Cited

U.S. PATENT DOCUMENTS

| | | |
|---|---|---|
| 4,145,406 A | 3/1979 | Schick et al. |
| 4,254,082 A | 3/1981 | Schick et al. |
| 4,687,732 A | 8/1987 | Ward et al. |
| 4,690,890 A | 9/1987 | Loor et al. |
| 4,792,521 A | 12/1988 | Shochat |
| 4,863,875 A | 9/1989 | Bailey et al. |
| 5,089,423 A | 2/1992 | Diamandis et al. |
| 5,108,896 A | 4/1992 | Philo et al. |
| 5,252,487 A | 10/1993 | Bacus et al. |
| 5,482,698 A | 1/1996 | Griffiths |
| 5,487,975 A | 1/1996 | Miller et al. |
| 5,620,845 A | 4/1997 | Gould et al. |
| 5,691,154 A | 11/1997 | Callstrom et al. |
| 5,719,063 A | 2/1998 | Block |
| 5,869,274 A | 2/1999 | Tsao et al. |
| 5,891,658 A | 4/1999 | Klainer et al. |
| 6,008,057 A | 12/1999 | Glass et al. |
| 6,252,053 B1 | 6/2001 | Ohbayashi et al. |
| 6,409,990 B1 | 6/2002 | Vera |
| 6,537,745 B2 | 3/2003 | Chien et al. |
| 6,580,056 B1 | 6/2003 | Tacha |
| 2002/0106685 A1 | 8/2002 | Henning et al. |
| 2002/0173053 A1 | 11/2002 | Damaj et al. |
| 2003/0017491 A1 | 1/2003 | Shi et al. |

FOREIGN PATENT DOCUMENTS

| | | |
|---|---|---|
| WO | WO 97/01758 | 1/1997 |
| WO | WO 2005/054860 A1 | 6/2005 |

OTHER PUBLICATIONS

Rami Suzuki, et al., "Proliferation and differentiation in the human breast during pregnancy", Differentiation, vol. 66, No. 2-3, XP-002522647, Oct. 2000, pp. 106-115.
Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.
David Y. Mason, et al., "Double immunofluorescence labelling of routinely processed paraffin sections", Journal of Pathology, vol. 191, No. 4, XP-002522649, Aug. 2000, pp. 452-461.
Susan Van Noorden., "Advances in immunocytochemistry", Folia Histochemica Et Cytobiologica, vol. 40, No. 2, XP-008104795, 2002, pp. 121-124.
Susan Van Noorden., "Immunocytochemistry for light microscopy a technical update", The biomedical Scientist, XP-002522654, Aug. 2003, pp. 808-811.
Chris M. Van der Loos, et al., "Immunohistochemical Detection of Interferon-γ: Fake or Fact?", The Journal of Histochemistry & Cytochemistry, vol. 49, No. 6, XP-002522653, Jun. 2001, pp. 699-709.
Brunangelo Falini, et al., "Double Labeled-Antigen Method for Demonstration of Intracellular Antigens in Paraffin-embedded Tissues", The Journal of Histochemistry and Cytochemistry, vol. 30, No. 1, pp. 21-26 (1982).
Bisgaard et al, Acta Histochemical et Cytochemica 29, 1996, pp. 738-739.
Sabattini et al, J. Clinical Patholgy, 51, 1998, pp. 506-511.
Ferri et al, J. Histochemistry & Cytochemistry 45, 1997, pp. 155-158.
Mason et al, J. Cancer Res. Clin. Oncol. 101, 1981, pp. 13-22.
Myers et al, J. Surg. Pathol. 1, 1995, pp. 105-113.
Anonymous, 1999-2007, Good's Buffers. USB Tech Library, Printed Oct. 11, 2007, from www.usbweb.com/reference2.asp?id_ref=23.

(Continued)

*Primary Examiner* — Mark Shibuya
*Assistant Examiner* — James L Grun
(74) *Attorney, Agent, or Firm* — Oblon, Spivak, McClelland, Maier & Neustadt, L.L.P.

(57) ABSTRACT

The present invention provide reagents and methods of using the reagents, for example, on automated staining devices, that facilitate detection of two or more antigens in a sample simply and efficiently.

13 Claims, No Drawings

(56) References Cited

OTHER PUBLICATIONS

Letter from Fisher Scientific, Jun. 15, 2006.
Tidman, et al., "Delineation of Human Thymocyte Differentiation Pathways Utilizing Double-Staining Techniques with Monoclonal Antibodies". Clinical and Experimental Immunology, 1981, vol. 45, pp. 457-467.
Hasui, et al., "Double Autoimmunostaining with Glycine Treatment", Journal of Histochemistry and Cytochemistry (2003) vol. 51, No. 9, pp. 1169-1176.
Nakane, P.K., "Simultaneous Localization of Multiple Tissue Antigens using the Peroxidase-Labeled Antibody Method: A Study on Pituitary glands of the Rat. Journal of Histochemistry and Cytochemistry", (1968), vol. 16, No. 9, pp. 557-560.
Krajewski, et al., "Detection of Multiple Antigens on Western Blots.", Analytical biochemistry (1996), vol. 236, pp. 221-228.
Boscato, et al. "Incidence and Specificity of Interference in Two-Site Immunoassays", Clinical Chemistry (1986), vol. 32, No. 8, pp. 1491-1495.
C.M. van der Loos, "Immunoenzyme Multiple Staining Methods", Microscopy Handbooks 45, (1999).
D.Y. Mason, et al. "Alkaline phosphatase and peroxidase for double immunoenzymatic labelling of cellular constituents", Journal of Clinical Pathology, (1978, 31, 454-460.
C.M. Van der Loos, et al, "Multiple immunoenzyme staining techniques Use of fluoresceinated, biotinylated and unlabelled monoclonal antibodies", Journal of Immunological Methods, 117 (1989), pp. 45-52.
Chris M. Van der Loos, et al. "An Immunoenzyme Triple-staining Method Using Both Polyclonal and Monoclonal antibodies from the same Species. Application of combined direct, Indirect, and Avidin-Biotin Complex (ABC) Technique", The Journal of Histochemistry and Cytochemistry, vol. 35, No. 11, pp. 1199-1204 (1987).
Chris M. Van der Loos, et al. "The Animal Research Kit (ARK) Can Be Used in a Multistep Double Staining Method for Human Tissue Specimens", The Journal of Histochemistry & Cytochemistry, vol. 48, (10): 1431-1437 (2000).
Chris M. Van der Loos, et al. "The use of enhanced polymer one-step staining reagents for immunoenzyme double-labelling", Histochemical Journal (28), pp. 709-714 (1996).
Chris M. Van der Loos, et al. "Use of commercially available monoclonal antibodies for immunoenzyme double staining", Histochemical Journal (20) pp. 409-413 (1988).
Chris M. Van der Loos, et al. "Practical suggestions for successful immunoenzyme double-staining experiments", Histochemical Journal (25), pp. 1-13 (1993).
Diane Trueman, et al., "An Automated Technique for Double Staining Rat and Rabbit Fetal Skeletal Specimens to Differentiate Bone and Cartilage", Biotechnic & Histochemistry, vol. 74, No. 2, pp. 98-104.
C. Knabe, et al. "A method for immunohistochemical detection of osteogenic markers in undecalcified bone sections", Biotechnic & Histochemistry (2006), 81(1):31-39.
Thomas F. Warner, et al., "Heparan Sulphate Proteoglycan in Scleromyxedema Promotes FGF-2 Activity", Patho. Res. Pract. 198:701-707 (2002).
Beata A. Wiatrowska, et al., "Cultured Anaplistic Cell Lines as Immunocytochemistry Controls: A Comparison of ThinPrep®—Processed Smears and Conventional Air-Dried Cytospins", Diagnostic Cytopathology, vol. 25, No. 5 (2001).
Jaroslav Mokry, "Versatility of Immunohistochemical Reactions: Comprehensive Survey of Detection Systems", ACTA MEDICA, 1996:39:129-140.
Shan-Rong Shi, et al. "Sensitivity and Detection Efficiency of a Novel Two-Step Detection System (Power Vision) for Immunohistochemistry", Applied Immunohistochemistry & Molecular Morphology 7(3):201-208, 1999.
DAKO datasheet, DuoFlex Cocktail, Code IC004 (119877-001).
BioGenex datasheet, Rabbit Anti-PIN4 Cocktail—AB448ME, Doc. No. 932-448ME Rev A, release date Aug. 17, 2007.
Abrahams, NA, et. al., Histopathology, 2002, 41, 35.
Adley, BP et. al., Am. J. Clin. Path., 2006, 126, 849.
Beach, R et. al., Am. J. Surg. Path., 2002, 26, 1588.
Bostwick, DG and Qian, J., Mod. Pathol., 2004, 17, 360.
DAKO Press Release Sep. 14, 2009, New Dupflex Cocktail Antibodies.
DAKO Screen Shot DuoFlex Cocktail, Anti-AMACR, Anti-Cytokeratin HMW, Anti-Cytoderatin 5/6.
DBBiosystems Datasheet, PIN-4, Mouse anti-P63, Mouse anti-Cytokeratin (HMW) and Rabbit anti-p504S (AMACR) Cocktail, (Research Use Only Data Sheet DS-PDM157-A).
Herawi, M and Epstein, JI, Am. J. Surg. Path., 2007, 31, 889.
Jiang, Z et. al., Am. J. Surg. Path., 2001, 25, 1397.
Jiang, Z et. al., Am. J. Clin. Path., 2004, 122, 275.
Jiang, Z et. al., Am. J. Clin. Path., 2005, 123, 231.
Luo, J et. al., Cancer. Res., 2002, 62, 2220.
Molinié, V. et. al., Mod. Pathol., 2004, 17, 1180.
Paner, GP, . et. al., Best Prac. in Diag. Immunohist.: Prostate, 2008, 132, 1388.
Rubin, MA et. al., JAMA, 2002, 287, 1662.
Sanderson, SO et. al., Am. J. Clin. Path., 2004, 121, 220.
Shah, RB et. al., Am. J. Surg. Path., 2002, 26, 1161.
Signoretti, S et. al., Am. J. Path., 2000, 157, 1769.
Tacha, DE and Miller, RT, Appl. Immunohistochem. Mol. Morph., 2004, 12, 75.
Tavora, F and Epstein, JI, Am. J. Surg. Path., 2008, 32, 1060.
Yang, Y et. al., Am. J. Path., 1997, 150, 693.
Zhou, M et. al., Am. J. Surg. Path., 2003, 27, 365.
Epstein, JI, and Netto, GJ., Biopsy interpretation of the prostate, 2008, Lippincott, Williams & Wilkins: Philadelphia, p. 99.
Office Action issued Sep. 27, 2010, in European Patent Application No. 05 723 587.1-1223, filed Feb. 24, 2005.
12 pages from catalog: "product information form the Sigma-Aldrich Online Catalog" at sigmaaldrich.com/.../ProductDetail.do?I . . . accessed Feb. 14, 2011.
8 pages from catalog: "product information form the Sigma-Aldrich Online Catalog" at sigmaaldrich.com/.../ProductDetail.do?1 . . . accessed Feb. 16, 2011.
Office Action issued Mar. 22, 2012 in European Application No. 05 723 587.1-1223.
Data Sheet Fast Red Stubsrate Pack and Compponents for Use with Alakline Phosphatase Detection Kits & BioGenex Automated Staining Systems (Doc. No. HK180, Rev. No. F112) Jul. 1, 2003 accessed from web.archive.org/web/20030701115828/http://www.biogenex.com/biogenex_h.html.
Vector Red Alkaline Phosphatase Substrate Kit I Cat. No. SK-5100, Oct. 31, 2000, accessed from web.archive.org/web/20031202200453/http://www.vector.labs.com/protocols.asp.
Cordell et al, Journal of Histochemistry and Cytochemistry, 1984, vol. 32, No. 2, pp. 219-229 online version http://jhc.sagepub.com/content/32/2/219.
Instructions for Universal Alkaline Phosphatase Immunostaining Kit (for Mouse and Rabbit Primary Antibodies) Cat. #KA-50F Apr. 7, 2003 Accessed from web.archive.org/web/20030407222427/http://dbiosys.com/new/index.asp?fuse=dsp_cat&id=5.
Elias, Immunohistopathology—A Practical Approach to Diagnosis, 2nd Ed., American Society for Clinical Pathology Press: Chicago, © 2003, p. 36.
Office Action issued Jun. 18, 2012 in European Application No. 11190842.2.
Extended European Search Report issued May 16, 2012, in Patent Application No. 11190842.2.
Partial Search Report issued Jan. 31, 2012 in European Application No. 11190842.2-1223.
Anonymous: "PIN cocktail-2 (P504S+p63)", Biocarta, May 4, 2003, pp. 1-3, XP 002667408, Retrieved from the Internet: URL:http://www.biocarta.com/TDS/PM205DSH.pdf [retrieved on Jan. 18, 2012].
Anonymous: "Double vision, the double stain, polymer detection system", Biocare Medical, Aug. 2, 2003, pp. 1-5, XP002667409, retrieved from the Internet: URL:http://web/archive.org/web/20030802112943/http://biocare.net/Detection.htm [retrieved Jan. 18, 2012].

(56) References Cited

OTHER PUBLICATIONS

Anonymous: "Double vision, the double stain, polymer detection system", Biocare Medical, Oct. 2, 2003, pp. 1-5, XP002667410, retrieved from the Internet: URL:http://web/archive.org/web/20031002060452/http://biocare.net/Detection.htm [retrieved Jan. 18, 2012].

Anonymous: "Double vision, the double stain, polymer detection system", Biocare Medical, Jan. 1, 2004, pp. 1-5, retrieved URL:http://web/archive.org/web/20040101180833/http://biocare.net/Detection.htm [retrieved Jan. 18, 2012].

Reis-Filho et al, Virchows Arch. (2003) vol. 443, pp. 122-132.

European Office Action Issued Mar. 19, 2013 in Patent Application No. 05 723 587.1.

IMMUNOASSAY REAGENTS AND METHODS OF USE THEREOF

BACKGROUND OF THE INVENTION

1. Field of the Invention

The present invention relates to the detection of antigens in a sample using antibody reagents.

2. Description of the Background

The evolving field of immunohistochemistry has led to simplified protocols with shorter incubation times, and automation. The ability to stain two or more antibodies on one tissue section has evolved as well. A double or triple stain assay would be much more practical for both pathologist and histo-technologist, reducing error, reducing reagents, reducing amount of tissue needed, and most important-time. Furthermore, this technology leads to a more practical method for a pathologist to make a diagnosis with antibodies that need to be stained in unison as well as situations where there is limit tissue.

In the past, double or triple stains were primarily performed in the research setting. However, the prior double and triple stained procedures required trained personnel, were technically difficult, time consuming, and in most cases, was not used on an automated immunostaining system. Therefore, the use of double or triple staining techniques is not often used in the clinical setting.

Previously, a typical 3-step avidin-biotin horseradish peroxidase (HRP) system was used for the first antibody sequence, followed by an elution (denaturing) step, and then a second antibody sequence with an alkaline phosphatase (AP) system. This product a brown (DAB) and red (Fast Red) color precipitate for each antigen, thus producing a double stain. If the tissue contained endogenous biotin, an avidin-biotin step was required. A double stain could require 30 to 40 steps and a triple stain could take 40 to 50 steps, depending on the complexity of the assay. Most automated immunohistochemistry stainers were not designed to do these complicated double stain assays. It also required a highly trained technician to properly titer each antibody sequence.

A biotin-free polymer detection kits for both HRP and AP detection system has been recently introduced (DakoCytomation; Zymed Laboratories). These kits eliminate the avidin-biotin blocking steps and require one step for detection versus two. However, depending on the immunostainer and the number of washes required, these kits still require significant technical expertise and IHC staining programming are not design adequately for double stains and especially triple stains. Also, lack of sensitivity with nuclear antigens have been reported with this kind of polymer kit. This new technology has been popular in the research arena, but has not been used much in clinical setting because of these difficulties.

The use of antibody cocktails has been used in the clinical setting for a number of years. LCA, AE1/AE3, CMV, and most recently, CD15, Pan Melanoma (HMB45+MART-1+ Tyrosinase) and PIN-4 (P504S+HMWCK+p63) are several cocktails that are being used on a routine basis in the clinical setting. Universal detection kits with both anti-mouse and anti-rabbit have also been used since the late 1980's.

Double and triple stain technology using immunohistochemistry in formalin-fixed paraffin-embedded tissues has also been used for many years. Double stains are accomplished by applying primary antibodies and detection in a sequence of steps to achieve multiple labeling on the same tissue. Various methods for detection used include fluorescence, immunoperoxidase, immunogold and in situ methods.

In view of the above, the disadvantages of the previous double stain technology have become apparent. Illustrative of these disadvantages is the typical procedure of the previous technology to perform a double stain immunoassay. For example, the sample is treated with Hydrogen Peroxide for 5 minutes followed by two optional protein block (5 to 10 minutes) and Avidin-Biotin block (20 to 40 minutes). Then, the primary antibody is applied for 30 to 60 minutes, linked for 10 to 20 minutes, labeled with, e.g., HRP for 10 to 20 minutes, treated with DAB for 5 minutes, and then denatured for 5 minutes. Subsequently, the second primary antibody is applied for 30 to 60 minutes, followed by an optional protein block for 5 to 10 minutes, linking for 10 to 20 minutes, and then labeling the second primary antibody, for example, with AP, for 10 to 20 minutes. The reactivity is detected by applying Fast Red for 10 to 20 minutes followed by counterstaining (plus bluing) for 30 and 60 seconds and coverslipping, which requires a water-base mounting media. The total time for this double stain procedure is about 3 to 4 hours with a total of 11-15 manual steps; plus 12 to 14 washes (32 maximum steps). Further, for a triple stain one would add 5 more steps (40+ maximum steps) and would take a total time of 4 to 5 hours.

Generally, diluting antibodies in a buffer and storing antibodies is known however, those dilutions typically were performed in phosphate buffered saline or other isotonic solution and may also have small quantities of bovine serum albumin and in some instances relatively small amounts of detergents such as Triton X-100 or NP-40 (Antibodies: A Laboratory Manual, Harlow and Lane, Cold Spring Harbor Laboratory Press, Cold Spring Harbor, N.Y., 1988; and Current Protocols in Molecular Biology, Ausebel et al (eds.), John Wiley and Sons, Inc. N.Y., 2001). However, the combination of reagents in a primary antibody cocktail as described as the present invention was not described previously. Furthermore, it was not known that these cocktails would stabilize the antibodies and permit the rapid and efficient staining with two or more antibodies.

SUMMARY OF THE INVENTION

Accordingly, the present invention provides reagents containing primary antibodies and a detection system, which accomplish these goals. Thus, the present invention provides a means to dramatically reduce the amount of steps required and provides the ability to perform automated immunoassays.

In one aspect of the present invention compositions comprising two or more antibodies mixed with various reagents are provided.

In another aspect of the present invention compositions comprising reagents suitable for the detection of the antibody containing reagents are provided.

In another aspect of the present invention, methods of detecting two or more antigens in a single sample using the compositions of the invention are provided. In one embodiment, the method can be performed on an automated device capable of staining and detecting the antigens in the sample.

In an additional aspect of the present invention is a denaturing solution that compensates for tissue pretreatment and methods of use in an antibody detection assay.

DETAILED DESCRIPTION OF THE INVENTION

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, 3$^{rd}$ Edition, Cold Spring Harbor Laboratory, Cold Spring Harbor, N.Y. (2001), Current Protocols in Molecular Biology, Ausebel et al (eds.), John Wiley and Sons, Inc., New York (2001), and the various references cited therein.

Primary Antibody Compositions

The present invention provides cocktailed primary antibodies, i.e., an antibody composition that are ready to use or concentrates). The advantages of providing such cocktails include one half to one third of the total number primary steps for performing a double staining procedure, i.e., staining with two antibodies; when using a primary cocktail of mouse and rabbit antibodies, the denaturing step may be omitted; a triple stain, i.e., staining with three antibodies, can be accomplished with 8 to 10 steps verses 16 to 24 steps in prior procedures, i.e., 2 to 2½ hours for the present invention versus 4 to 5 hours in prior procedures; both double and triple staining procedures can be fully automated; it enables the reduction in the number of slides to be processed; permits a higher level of quality control, for example, when the stained samples are viewed by a pathologist. Overall the present invention also reduces total costs, which is a significant factor in processing samples in the clinical setting.

The present invention is applicable anywhere antibody staining is conventional employed. For example, double, triple and quadruple staining can be performed in Immunocytochemistry; Immunohistochemistry; Frozen sections; Formalin-fixed paraffin embedded tissues; Cell Cultures; Tissue or cell culture microarrays; Paraffin-embedded tissues (any fixation protocol); Cell smears; Cell blocks; Cytospins; PAP smear; Blood smears; and Touch Preps. In certain embodiments, the sample is attached to a solid support, for example, a glass slide, ELISA plate, culture dish, glass dish, plastic dish, glass well, or plastic well.

The antibody compositions or cocktails of the present invention comprise two or more antibodies in double staining procedures, and, for example, in triple staining procedures the compositions would contain three antibodies, etc. The antibodies can are preferably different in that the antibodies react with different antigens and/or different isoforms or epitopes of a particular protein/antigen in a single sample. The antibodies can be monoclonal or polyclonal and can be obtained according to standard antibody technology known in the art. The antibodies can be from any species, such as rat, horse, goat, rabbit, human, mouse, etc. In a preferred embodiment, the antibodies are from rabbit, goat, and/or mouse. In another preferred embodiment, the at least two of the antibodies in the composition are from different sources or species. In another preferred embodiment, at least one of the antibodies in the primary antibody cocktails is a rabbit antibody, and more preferably a rabbit monoclonal antibody. For example, Rabbit monoclonals antibodies can be obtained from Lab Vision Corp; Fremont, Calif.)

The antibodies can be diluted in one or more of the buffer systems described herein, for example, at least 1:50 and preferably from about 1:50 to 1:6000, including 1:100, 1:150, 1:200, 1:250, 1:300, 1:350, 1:400, 1:450, 1:500, 1:550, 1:600, 1:650, 1:700, 1:750, 1:800, 1:850, 1:900, 1:1000, 1:1100, 1:1200, 1:1300, 1:1400, 1:1500, 1:1600, 1:1700, 1:1800, 1:1900, 1:2000, 1:2100, 1:2200, 1:2300, 1:2400, 1:2500, 1:2600, 1:2700, 1:2800, 1:2900, 1:3000, 1:3100, 1:3200, 1:3300, 1:3400, 1:3500, 1:3600, 1:3700, 1:4000, 1:4100, 1:4200, 1:4300, 1:4400, 1:4500, 1:4600, 1:4700, 1:4800, 1:4900, 1:5000, 1:5100, 1:5200, 1:5300, 1:5400, 1:5500, 1:5600, 1:5700, 1:5800, 1:5900 and all ranges and values therebetween.

According to the invention, the two or more antibodies are prepared in a composition comprising a buffer system that stabilizes the antibodies and facilitates a faster detection after the antibodies have bound to the antigen.

In one embodiment, the composition of the two or more antibodies contains, in one embodiment, sodium phosphate monobasic, monohydrate; potassium phosphate dibasic, trihydrate; Polyoxyethylenesorbitan monolaurate (Tween® 20), bovine serum albumin (BSA), sodium azide, and water and wherein the pH is about from 5.5 to 6.5 and preferably 6.0. In a preferred embodiment, this composition contains approximately 1.5 to 3.0 g/l sodium phosphate monobasic, monohydrate; 0.5 to 0.6 g/l potassium phosphate dibasic, trihydrate; 0.5 to 1.5 ml/l Polyoxyethylenesorbitan monolaurate (Tween® 20) 50 to 100 ml/l of 5% bovine serum albumin (BSA), 0.5 to 1.5 g/l sodium azide, 0.005 g/l, and the remainder water. In a more preferred embodiment, this composition contains approximately 2.4 g/l sodium phosphate monobasic, monohydrate; 0.56 g/l potassium phosphate dibasic, trihydrate; 1 ml/l Polyoxyethylenesorbitan monolaurate (Tween® 20), 100 ml/l of 5% bovine serum albumin (BSA), 0.9 g/l sodium azide, and the remainder water. In one embodiment, bromthymol blue may be added to these compositions in an amount of from 0.0001 to 0.001 g/l, and preferably 0.005 g/l.

In second embodiment, the composition contains PBS, sodium azide, Polyoxyethylenesorbitan monolaurate (Tween® 20), BSA and the remainder water, and where the pH is from about 7.0 to about 6.5 and preferably about 7.3. In a preferred embodiment, this composition contains 40 to 60 ml/l 10×PBS, 0.75 to 1.25 g/l sodium azide, 0.1 to 0.3 ml/l Polyoxyethylenesorbitan monolaurate (Tween® 20), 45 to 65 g/l BSA, and the remainder water. In a further preferred embodiment, this composition contains 50 ml/l 10×PBS, 0.9 g/l sodium azide, 0.2 ml/l Polyoxyethylenesorbitan monolaurate (Tween® 20), 55 g/l BSA, and the remainder water.

In a third embodiment, the composition contains Tris-HCl, sodium azide, BSA, hydrochloric acid and the remainder water at a pH of from about 5.7 to about 6.5 and preferably about 6.2. In a preferred embodiment, this composition contains 3.0 to 4.0 g/l Tris-HCl, 0.75 to 1.2 g/l sodium azide, 7.5 to 12.5 g/l BSA, 0.2 to 0.3 ml/l 25% hydrochloric acid, and the remainder water. In a further preferred embodiment, this composition contains 3.5 g/l Tris-HCl 0.9 g/l sodium azide, 10 g/l BSA, 0.25 ml/l 25% hydrochloric acid, and the remainder water.

In a fourth embodiment, the composition contains 1 part of solution A and 1 part of solution B where solution A contains PBS, preservative (Proclin™ 950), Polyoxyethylenesorbitan monolaurate (Tween® 20), purified casein, Prionex (purified Type A gelatin), and water and solution B contains sodium phosphate monobasic, monohydrate; potassium phosphate dibasic, trihydrate; Polyoxyethylenesorbitan monolaurate (Tween® 20), bovine serum albumin (BSA), sodium azide, and water and wherein the pH is about 5.75 to 6.25 and preferably a pH of 6.0. In a preferred embodiment of this composition, solution A contains 75 to 125 ml/l 10×PBS, 2.5 ml/l preservative (Proclin™ 950), 0.25 to 0.75 ml/l of 50% Polyoxyethylenesorbitan monolaurate (Tween® 20), 2.5 to 7 g/l purified casein, 2.0 to 3.0 ml/l Prionex (purified Type A gelatin), and water; and solution B contains 2.0 to 3.0 g/l sodium phosphate monobasic, monohydrate; 0.5 to 0.6 g/l potassium phosphate dibasic, trihydrate; 0.75 to 1.25 ml/l Polyoxyethylenesorbitan monolaurate (Tween® 20), 75 to 125 ml/l of 2.5 to 7.5% bovine serum albumin (BSA), 0.7 to 1.1 g/l sodium azide, and the remainder water. In a further preferred embodiment of this composition solution A contains 100 ml/l 10×PBS, 2.5 ml/l preservative (Proclin™ 950), 0.5 ml/l of 50% Polyoxyethylenesorbitan monolaurate (Tween® 20), 5 g/l purified casein, 2.5 ml/l Prionex (purified Type A gelatin), and water; and solution B contains approximately 2.4 g/l sodium phosphate monobasic, monohydrate; 0.56 g/l potassium phosphate dibasic, trihydrate; 1 ml/l Polyoxyethylenesorbitan monolaurate (Tween® 20), 100 ml/l of 5% bovine serum albumin (BSA), 0.9 g/l sodium azide, and the remainder water. In a further preferred embodiment, solution B also contains 0.0001 to 0.001 g/l bromthymol blue, preferably 0.005 g/l bromthymol blue.

In a fifth embodiment, the compositions of primary antibodies comprises sodium phosphate monobasic, monohydrate; potassium phosphate dibasic, trihydrate; Polyoxyethylenesorbitan monolaurate (Tween® 20), bovine serum albumin (BSA), sodium azide, and water and wherein the pH is about from 5.5 to 6.5 and preferably 6.0 and from 40 to 60% glycerol, preferably 50% glycerol. In a preferred embodiment, this composition contains approximately 1.5 to 3.0 g/l sodium phosphate monobasic, monohydrate; 0.5 to 0.6 g/l potassium phosphate dibasic, trihydrate; 0.5 to 1.5 ml/l Polyoxyethylenesorbitan monolaurate (Tween® 20), 50 to 100 ml/l of 5% bovine serum albumin (BSA), 0.5 to 1.5 g/l sodium azide, 0.005 g/l, and the remainder water. In a more preferred embodiment, this composition contains approximately 2.4 g/l sodium phosphate monobasic, monohydrate; 0.56 g/l potassium phosphate dibasic, trihydrate; 1 ml/l Polyoxyethylenesorbitan monolaurate (Tween® 20), 100 ml/l of 5% bovine serum albumin (BSA), 0.9 g/l sodium azide, and the remainder water. In one embodiment, bromthymol blue may be added to these compositions in an amount of from 0.0001 to 0.001 g/l, and preferably 0.005 g/l.

Non-limiting Examples of primary antibodies and antibody combinations useful in the present invention include those listed in below (AP=Alkaline phosphtase, HRP=Horseradish Peroxidase, Ms+Mouse): T-cell and apoptosis marker (CD3 [PS1]; Caspase-3 (Polyclonal)); B-cell vs T-cell marker (CD20 [L26]; CD3 (Rabbit monoclonal) [SP11]); B-cell vs T-cell marker (CD20 [L26]; CD3 [PS1]); Blood Vessels and cell proliferation (CD31[JC/70A]; Ki-67 (Rabbit monoclonal) [SP6]); Dermatopathology Marker (CD34 [QBEnd/10]; Factor XIII Subunit a (polyclonal)); Colon cancer verses breast or lung cancer (CDX2 [CDX2-88]; CK7 [K72.7]); G.I vs Lung or breast (CK7 [K72.7]; CK20 [Ks20.8]); Kappa/Lambda (Kappa [KDB-1]; Lambda (polyclonal)); Cell proliferation and Apoptosis marker (Ki-67 [MIB-1]; Caspase-3 (polyclonal)); Cell proliferation and Apoptosis marker (M30 (CM224A); i-67 (rabbit monoclonal) [SP6]); Screening Marker (LCA [PD7/26/16]+2B11; S-100 (polyclonal)); Screening Marker (LCA [PD7/26/16+ 2B11]; S100 (Polyclonal); CK8/18 [5D3]) B-cell and cell proliferation (CD20 [L26]; Ki-67 (rabbit monoclonal)[SP6]; Pan Melanoma; Tyrosinase [T311]; S-100 (rabbit polyclonal); MART-1 [M2-7C10+M2-9E3] or A103); Invasive breast cancer (p63 [BC4A4]; CK5 [XM26]; CK8/18 [5D3]); PIN Cocktail-2 (p63 [BC4A4]; P504S (rabbit monoclonal) [P504S]); PIN Cocktail-4 (p63 [BC4A4]; HMW CK [DE-SQ]; P504S (rabbit monoclonal)); Mesothelioma marker (CK5/6 [CK5/6.007]; Calretinin (rabbit monoclonal) [SP13]); Breast cancer prognostic marker (Estrogen receptor [6F11]; Ki-67 (rabbit monoclonal)); Breast cancer prognostic marker (Estrogen receptor (rabbit monoclonal)[SP1]; Ki-67 [MIB-1]); Prognostic breast cancer marker (CK5 [XM26]; CK17 [Ks17.E3]; CK8/18 [5D3]); Liver cancer marker (CD10 [56C3]; Prostate Specific Antigen (PSA) (polyclonal); Hepatic Specific Antigen (HSA) [OCH1E5]; Pan Neuroendocrine; Chromogranin A [LK2H10+PHE5]; Synaptophysin (Rabbit Monoclonal) [SP11]); Adenocarcinoma vs Squamous Cell Carcinoma (HMW CK [DE-SQ] or [34βE12]; LMW CK (CK8/18) [5D3]); B-cell and Apoptosis Marker (CD20 [L26]; Caspase-3 (polyclonal)); T-cell and cell proliferation marker (CD3 [PS1]; Ki-67 (Rabbit Monoclonal)[SP6]); Chronic Lymphocytic Leukemia (CD5 (rabbit monoclonal) [SP9]; PAX-5 [BC/24]); and T-cell Marker (CD4 [1F6]; CD8 (polyclonal))

Further non-limiting examples of antibody cocktails (compositions) are listed in the table below (M=mouse; R=rabbit):
LCA (M)+S100 (R)
LCA (M)+S100 (R)+CK8/18 (M) or Pan Cytokeratin (Triple stain)
Kappa (M) and Lambda (R)
L26 (M) B-cell+CD3 (R) T cell (Lymphoma)
L26 (M)+Ki-67 (R)
CD3 (M)+Ki67 (R)
Ki-67 (M)+Caspase-3 (R)
HMWCK (M)+LMWCK (M)
CK7 (M)+CK20 (M)
CK7 (M)+CDX-2 (M)
ER (M)+Ki-67 (R)
P504S (R)+HMWCK+p63 (M) (PIN)
CK5+p63+CK8/18 (Breast cancer)
CK5/6 (M)+Calretinin (R)
MART-1+Tyrosinase+S100 (R) (Melanoma)
CD34 (M)+Factor XIIIa (R)
Apoptotic/CK18 (M)+Ki-67 (R)
CD31 (M)+Ki-67 (R)
CD10+HSA+PSA (Liver cancer and metastasis) (Triple Stain)
PAX-5+CD 5 (leukemia)
CK/5+CK17+CK8/18
CK5/6+Calretinin
ER+Ki-67
CDX2+CK7

Secondary Antibody Compositions

The use of secondary antibodies to detect the binding between a primary antibody and an antigen are known (Antibodies: A Laboratory Manual, Harlow and Lane, Cold Spring Harbor Laboratory Press, Cold Spring Harbor, N.Y., 1988; and Current Protocols in Molecular Biology, Ausebel et al (eds.), John Wiley and Sons, Inc. N.Y., 2001). However, in the present invention the formulation of a composition of a secondary antibody composition capable of detecting two different antibodies at the same time was not known.

Accordingly, one embodiment of the present invention is to provide a secondary antibody composition coupled with a biotin-free polymer conjugated to an enzyme or other detectable moiety capable of being detected using various chromogens and/or other detectable moieties. Conjugating detectable moieties or enzyme systems to secondary antibodies is known (Antibodies: A Laboratory Manual, Harlow and Lane, Cold Spring Harbor Laboratory Press, Cold Spring Harbor, N.Y., 1988; and Current Protocols in Molecular Biology, Ausebel et al (eds.), John Wiley and Sons, Inc. N.Y., 2001).

The secondary antibodies are raised to react with the primary antibody based on the species origin of the primary antibody, e.g., if the primary antibody is a mouse antibody then the secondary antibody would be, for example, a rabbit anti-mouse antibody. In the present invention, the two or more secondary antibodies to visualize the binding between the two or more primary antibodies and the two or more antigens may be from the same source species or from different species. However, the two or more secondary antibodies are preferably coupled to a detectable moiety such as horseradish peroxidase (HRP) and alkaline phosphatase (ALP or AP) and in a particularly preferred embodiment; at least a first secondary antibody contains a detectable moiety that is different from the detectable moiety on a second secondary antibody. In one aspect of the present invention, the detectable moiety is poly-HRP or a poly-ALP and is described in Shi et al ((1999) Appl. Immuno & Mol. Morph. 7(3):201-208).

In accordance with the present invention, the secondary antibody composition described above, e.g., containing two or more secondary antibodies specific for the primary antibody composition, is contained in a buffer system suitable to stabilize the HRP and the AP moieties coupled to the secondary antibodies. In one aspect of this embodiment, the buffer system is a Tris buffer system, which may also contain a preservative that prevents microbial growth and does not result in any appreciable degradation of the detectable moieties. In one embodiment, the preservative is Proclin®.

In another embodiment, the buffer system comprises a solution of Tris buffer at a pH of from 7.3 to 7.9, Polyoxyethylenesorbitan monolaurate (Tween® 20) and goat serum. In a preferred embodiment, the secondary antibody composition comprises 0.8 to 1.2 M Tris buffer, pH from 7.3 to 7.9 with 0.025 to 0.075% Polyoxyethylenesorbitan monolaurate (Tween® 20) and 2.5 to 3.5% goat serum; and more preferably the secondary antibody composition comprises 0.1M Tris buffer, pH 7.6 with 0.05% Polyoxyethylenesorbitan monolaurate (Tween® 20) and 3% goat serum. In an alternative embodiment, the above composition may also contain tris-buffered saline (TBS) in amounts from 30 to 37 ml of 10×TBS/1, preferably 34 ml 10×TBS/l.

In a preferred embodiment, a conjugated goat anti-mouse poly-alkaline phosphatase (ALP) and a conjugated goat anti-rabbit poly-horseradish peroxidase (HRP) are used as secondary antibodies and react with both heavy and light chains on mouse and rabbit IgG The ALP- and HRP-polymerization provides a significant increase in staining sensitivity when compared to other conventional ALP- or HRP-conjugated secondary antibodies. Avidin-biotin blocking procedures are not necessary when using the conjugated secondary antibodies. Obviously then, the primary antibody cocktail will contain a rabbit and a mouse antibody.

In one embodiment of the present invention, chromogens are used to detect the antibody-antigen complex. Chromogens have improved dramatically over the last 5 years. In the past, several chromogens required a water-soluble mounting media and/or faded over time. The new generation of chromogens are permanent and do not fade. They come in several different colors. It is now easy to achieve four different chromogens on a single section. For example, chromogens useful in HRP Systems include, DAB (which appears brown), AEC (which appears brick red), and Bajoran Purple (which appears lavender to dark purple). For example, chromogens useful for Alkaline Phosphostase System include Fast Red (which appears pink to fuchsia), and Ferangi Blue (which appear royal blue).

Bajoran Purple is a permanent chromogen and is compatible with streptavidin horseradish peroxdase. Bajoran Purple is not soluble in alcohol or xylene and can be coverslipped just like DAB. When in the presence of a peroxidase enzyme, Bajoran produces lavender-purple stain.

3,3' Diaminobenzidine (DAB) is a widely used chromogen for immunohistochemical staining and immunoblotting. When in the presence of peroxidase enzyme, DAB produces a brown precipitate that is insoluble in alcohol and xylene. In a preferred embodiment, DAB is used with an enhanced to add contrast and increase staining intensity, such as for example DABENHANCER (BIOCARE Medical).

Fast Red is a widely used chromogen for immunohistochemical staining. When in the presence of alkaline phosphatase (AP) enzyme, Vulcan Fast Red produces a bright fuchsin-red precipitate that is insoluble in organic solvents and can be coverslipped with a permanent mounting media. When using an alkaline phosphatase system, tris buffer (pH 7.6) rather than PBS should be used as a rinsing buffer.

When in the presence of alkaline phosphatase (AP) enzyme, Ferangi Blue produces a bright royal blue precipitate that is insoluble in organic solvents—and can be coverslipped with a permanent mounting media. When using an alkaline phosphatase system, tris buffer (pH 7.6) rather than PBS should be used as a rinsing buffer.

In preferred embodiments, counterstains are used to visualize the staining patterns of the antibody-antigen complex. Non-limiting examples of those counterstains include Hematoxylin, Nuclear Fast Red, Methyl Green, and Methyl Blue.

In a set of preferred embodiments, cocktails of primary antibodies diluted in various buffers (referred to below as 1-5 corresponding to the first to fifth embodiments of the primary antibody cocktails above, combined with various chromogens are described below:

Methods of Performing an Immunoassay

To perform an immunoassay using the compositions of the present invention, a sample can be first contacted with a primary antibody composition, i.e., containing two or more primary antibodies and subsequently with a cocktailed detection reagent, i.e., containing two or more secondary antibodies coupled to detectable moieties. In a preferred embodiment of this method, the detectable moieties are at least AP and HRP, more preferably poly (AP) and poly (HRP). The antibody staining method of the present invention is different from prior staining protocols used previously because prior to the present invention performing staining of a sample with two or more antibodies required the application of the first primary antibody followed by detection of this antibody, a subsequent denaturing step to prepare the sample to receive a second primary antibody, then applying a second primary antibody followed by detection of this antibody, etc.

In a further embodiment of the antibody staining method of the present invention, a second composition of primary antibody, either containing a single primary antibody or a cocktail of 2 or more antibodies is added to the same sample following the detection of the first composition of cocktailed primary antibodies. Subsequently, the second composition of primary antibodies is detected using the detection reagents, secondary antibodies and detectable moieties as described herein.

In further embodiments of performing a double stain (or an immunoassay with two different antibodies) using the antibody compositions and the detection reagents of the present invention the following protocol can be employed, washing steps are employed between the various steps as is typically performed in an immunoassay. In some instances it may be preferable to pretreat the sample with a peroxide to facilitate antigen retrieval and/or enzyme digestion, however, as is appreciated by one of skill in the art some retrieval solutions block peroxidase and therefore the peroxide treatment would not be performed. In addition, in some instances recognized by the skilled artisan, it may be helpful to perform a protein-blocking step to minimize non-specific binding of the antibodies to the sample. If the protein blocking step is used it is typically conduced for about 10 minutes.

The primary antibody cocktail is applied to the sample to be assayed, typically from about 30 to about 60 minutes after which time a secondary-HRP-ALP Polymer cocktail is applied for about 20 to about 30 minutes. To visualize the antibody-antigen complexes a first chromogen, e.g., DAB is applied for about 5 minutes followed by applying a second chromogen, e.g., fast red for about 10 minutes. In preferred embodiments of the present invention, the sample is then counterstained, e.g., with progressive hematoxylin, for approximately 30 seconds to about one minute to facilitate better visualization of the stained antigen. The sample, if on a slide can then be covered with a coverslip to preserve the stained sample. Thus, this procedure can be performed in approximately 2 to 2½ hours requiring only about 5 to 7 steps and 6 to 8 wash steps.

To perform a triple stain (or an immunoassay with three different antibodies) using the antibody compositions and the detection reagents of the present invention the following protocol can be employed, washing steps are employed between the various steps as is typically performed in an immunoassay. In some instances it may be preferable to pretreat the sample with a peroxide to facilitate antigen retrieval and/or enzyme digestion, however, as is appreciated by one of skill in the art some retrieval solutions block peroxidase and therefore the peroxide treatment would not be performed. In addition, in some instances recognized by the skilled artisan, it may be helpful to perform a protein-blocking step to minimize non-specific binding of the antibodies to the sample. If the protein blocking step is used it is typically conduced for about 10 minutes.

The primary antibody cocktail is applied to the sample to be assayed, typically from about 30 to about 60 minutes after which time a secondary-HRP-ALP Polymer cocktail is applied for about 20 to about 30 minutes. To visualize the antibody-antigen complexes a first chromogen, e.g., DAB is applied for about 5 minutes followed by applying a second chromogen, e.g., fast red for about 10 minutes. Then the sample is denatured using the appropriate denaturing solution for approximately 2 to 10 minutes (in some embodiments, the use of a graded dilution of the denaturing solution may be employed for about 5 minutes). A third primary antibody is applied to the sample for about 30 minutes and then a goat anti-mouse or rabbit HRP or AP Polymer is applied for about 20 to 30 minutes. A chromogen is applied, which is purple or blue, for 5 minutes. In preferred embodiments of the present invention, the sample is then counterstained, e.g., with progressive hematoxylin, for approximately 30 seconds to about one minute to facilitate better visualization of the stained antigen. The sample, if on a slide can then be covered with a coverslip to preserve the stained sample. Thus, this procedure can be performed in approximately 2½ to 3 hours requiring only about 9 to 11 steps and 9 to 11 wash steps.

In a similar manner as described above, immunoassays using four, five, six, etc. antibodies may be employed to visual various antigens in a given sample. When performing the above protocols using an alkaline phosphatase detection system, it is preferable to use a TBS wash buffer rather than a PBS-based wash buffers. In a similar manner, when performing the immunoassay according to the invention, the sample pretreatment must be taken into consideration. In preferred embodiments, the two or more antibodies should require the same sample pretreatment, for example, pretreatments such as none, digestion, and antigen retrieval (e.g., using low and high pH solutions). In some embodiments, no pretreatment procedure can be used for the first antibody composition (e.g., containing two or more antibodies) and then an antigen retrieval procedure can be used for the denaturing step and then the third antibody or second antibody composition. In some embodiments, antigen retrieval can be used before or after enzyme digestion. If using digestion after antigen retrieval, pepsin or trypsin is preferably used for 30 seconds; or a highly diluted trypsin can be used for 5 minutes at room temperature on automated stainers.

In further preferred embodiments of the invention, a denaturing step is employed when two sequential antibodies and detection systems are used. The denaturing step destroys (elution) the IHC steps of the protein block, primary antibody, secondary antibody, and label from the first antibody sequence. This denaturing step facilitates clean staining, i.e., preventing/minimizing the second antibody sequence from cross-reacting with the first antibody sequence. Depending on the pretreatment that is employed (none, digestion, or antigen retrieval), the time and/or concentration of the denaturing solution should vary. In the past, this procedure was not fully understood. This caused inconsistent staining and inaccurate staining. Typically in the past, laboratories used 0.5 to 1% HCL in water or 70% alcohol for 5 minutes.

A preferred denaturing solution comprises 1 part of solution A to 3 parts of solution B is also provided. Solution A contains 1.1 to 1.3% hydrochloric acid, 0.020 to 0.030% preservative (Proclin™ 300), and the balance water. Solution B contains 0.1 to 0.3% Polyoxyethylenesorbitan monolaurate (Tween® 20), about 0.2 to 0.3% preservative (Proclin 300) and the balance water. In a preferred embodiment, solution A contains 1.2% hydrochloric acid, 0.025% preservative (Proclin™ 300), and the balance water; and solution B contains about 0.2% Polyoxyethylenesorbitan monolaurate (Tween® 20), about 0.25% preservative (Proclin 300) and the balance water. A preferred blocking reagent contains 10% 10×PBS, 0.25% preservative (Proclin 950), 0.01% 50% solution of Polyoxyethylenesorbitan monolaurate (Tween® 20), 50 grams purified casein, 0.25% Prionex (purified type A gelatin), and the balance water. In one embodiment of antibody staining with at least two antibodies, the process entails contacting the sample with a first antibody, and subsequent secondary antibody and detection reagents, e.g., chromogens, adding the denaturing solution to the sample, and then contacting the sample with a second antibody with subsequent secondary antibody and detection reagents. The staining patterns can then be visualized. This process may be repeated to visualize, 3, 4, 5, etc. total antibodies on single sample.

Automated Applications

The unique formulations and ease of use of the antibody cocktail and/or detection reagents and/or other regents useful for the immunoassay facilitate performing the immunoassay in one or more automated devices designed to detect antibody staining patterns in a sample. In particular, the compositions of the present invention enable automation of double, triple, quadruple, etc. antibody detections that were difficult and in some instances even impossible with reagents known previously.

In another embodiment of the invention, the method described herein can be applied in the immuno-analysis of tissue microarrays. Tissue microarrays are known in the art and typically contain anywhere from 50 to 500 tissues on a single slide. The advantage of the present invention in the immuno-analysis of the tissue arrays is that the assay can be performed on numerous slides, e.g., 36 to 60 slides, on an automated staining apparatus and perform double, triple, quadruple, etc. stains on each slide. Another advantage of being able to perform such multiple stains on a given slide is cost since the tissue microarray slides typically cost up to $500.

In one embodiment, a low temperature antigen retrieval protocol can be performed. The low temperature antigen retrieval protocol involves preparing the tissue sample to the substrate, e.g., glass slide prior to staining. The low temperature method produced superior morphology as well as help secures precious tissues to the substrate. Thus, in this embodiment, the sample is treated, prior to staining, at a temperature from 65° C. to 80° C. and preferably about 75° C. Typically the sample is treated overnight. In a particularly preferred embodiment, the sample is treated with a device according to the description in U.S. Pat. No. 6,580,056, the entire contents of which are incorporated herein by reference.

Examples of such automated devices useful according to the present invention include, but are not limited to, BioGenex 16000™ (Biogenex), Dako Autostainer (DakoCytomation) Nemesis™ (BIOCARE), and those from Ventana Medical Systems (Capillary gap stainer, NexES and Benchmark).

For example, an automated double staining procedure using one of the above, e.g., Dako autostainer, is as follows. The sample is can be optionally blocked in hydrogen peroxide for 5 minutes, the sample is treated in a Biocare Decloaker for HIER, background blocking can be attained by adding Background Sniper (Biocare Medical) for 7 minutes and then blown off. A double stain primary antibody cocktail is added to the sample for 30 to 45 minutes and then rinsed; a secondary antibody composition is added for 25 minutes and then rinsed. DAB Chromogen for 5 minutes, rinse and Fast Red chromogen for 10 minutes. The sample is then ready for visualization and analysis.

Kits

The present invention also provides kits for immunoassaying a sample containing the antibody cocktail and/or detection reagents and/or other regents useful for the immunoassay. In a preferred embodiment, the kit also comes with instructions to use the immunoassay reagents.

EXAMPLES

Example 1

A double stain protocol for PIN-4 cocktail (P504S+HMW CK+p63)
1. After the sample is mounted on the slide, it is deparaffinized down to water
2. The antigens are heat retrieved in Reveal or BORG DECLOAKER (Biocare Medical) using a steamer for 60 minutes, or alternatively in a Digital Decloaking Chamber (Biocare Medical) for 30 seconds to 5 minutes.
3. A Protein Block in 4 drops (approx. 150 ul.) using of BACKGROUND SNIPER (Biocare Medical) is applied to the sample for 5-10 minutes. The sample is washed well.
4. The primary antibody PIN-4 Cocktail is applied for 30 to 60 minutes.
5. The sample is washed in two changes of 1× Immunocare TBS (Biocare Medical) for 2 minutes each.
6. Four drops of Goat anti-Mouse (ALP) and Goat anti-Rabbit (HRP) cocktail is added. Incubate for 30 minutes Drain Slides.
7. Wash in two changes of 1× Immunocare TBS wash Buffer (Biocare Medical) for two minutes each. Drain Slides.
8. Prepare DAB Chromogen Substrate by adding 1 drop of DAB Chromogen to 1.0 ml of Substrate Buffer and mix well. Apply four drops of the DAB Chromogen Substrate to the sample and develop for 2-3 minutes at room temperature. (DAB Sparkle (Biocare Medical) may be used for enhancement.)
9. The sample is washed in deionized. water. Check specimen under microscope. If it is under-developed DAB Chromogen substrate can be reapplied for another 2 minutes. Rinse in deionized water.
10. Wash in two changes of 1× Immunocare TBS wash Buffer (Biocare Medical) for two minutes each. Drain Slides.
11. Apply 4 drops of Vulcan Fast Red™ Chromogen Substrate (Biocare Medical) for 5-10 minutes. Rinse in deionized water. Place specimen under microscope and check for light staining. Only if the stain is too light, apply Vulcan Fast Red™ (Biocare Medical) for another 5 minutes and rinse again in deionized water.
12. Add 4 drops of Cat Hematoxylin (Biocare Medical) for 30-60 seconds. Wash in tap water.
13. Blue nuclei in 1×PBS wash buffer for 1 minute. Drain slides.
14. Wash in tap water and rinse in deionized water.
15. Dehydrate in 3 changes of 100% alcohol and clear in 3 changes of xylene.
16. Mount and coverslip.

Example 2

CK5+p63+CK8
Applying CK5+P63 with a Secondary Polymer HRP/DAB
1. Deparaffinize down to water
2. Heat retrieve in Decloaking Chamber (Biocare Medical) for 2-5 minutes.
3. Come back with a rinse in 1× IMMUNOCARE TBS (Biocare Medical) wash buffer.
4. Protein block for 10 minutes with BACKGROUND-SNIPER (Biocare Medical). Drain protein blocker.
3. Dilute CK5 1:200 and p63 1:500 in Van Gogh Yellow (Biocare Medical). Incubate for 30 minutes.
4. Wash in two changes of 1×TBS wash buffer for 2 minutes each. Drain slides.
5. Apply 4 drops of Goat-anti-Mouse-HRP (Polymer) and incubate for 25 minutes. Wash in 2 changes of 1×TBS wash buffer for 2 minutes each. Drain slides
6. Prepare Cardassain DAB Chromogen Substrate (Biocare Medical): Add 1 drop of DAB Chromogen A and B solutions to 1.0 ml of Substrate Buffer. Mix Well. Apply four drops of the DAB Chromogen Substrate. Develop for 2-5 minutes at room temperature.
9. Wash in deionized water. Check specimen under microscope (manual method only). If it is under-developed you can re-apply DAB Chromogen Substrate for another 2-4 minutes. Rinse in deionized water
6. Dip section into 0.5% HCL in 70% alcohol 2 to 5 minutes. Rinse well with TBS wash buffer.

Applying CK8/18 with a Polymer Second Antibody with a ALP/Fast Red Kit
1. Dilute CK 8/18 1:100 Van Gogh Yellow (Biocare Medical). Incubate for 30 minutes.
2. Wash in two changes of 1× Immunocare TBS (Biocare Medical) for 2 minutes each.
3. Apply four drops of Goat anti-Mouse-ALP (Polymer). Incubate for 20 minutes.
4. Wash in two changes of 1× Immunocare TBS (Biocare Medical) wash Buffer for two minutes each. Drain Slide.

5. Apply 4 drops of Vulcan Fast Red Chromogen Substrate (Biocare Medical) for 10 minutes. Rinse in deionized water. Place specimen under microscope and check for light staining (manual method only). If the stain is too light, apply Vulcan Fast Red Substrate for another 5 minutes and rinse again in deionized water.
6. Add 4 drops of CAT Hematoxylin for 30-60 seconds. Wash in tap water.
7. Blue nuclei in 1×PBS wash buffer for 1 minute. Drain slides.
8. Wash in tap water and rinse in deionized water.
9. Dehydrate in 3 changes of 100% alcohol and clear in 3 changes of xylene.
10. Mount and coverslip.

Example 3

Tissue Preparation.

All tissues were formalin-fixed paraffin-embedded and sectioned at 4 microns. Section were dried at 37° C. for 30 minutes and then dried at 60° C. for 30 minutes. Sections were immediately taken out of the oven and deparaffinized in Slide Brite, (BIOCARE) and then hydrated through a grades series of alcohol. All tissues were placed in a 3% hydrogen peroxide bulk solution for 5 minutes to quench endogenous peroxidase activity. The following tissues were used for double and triple stains: tonsil, colon cancer, liver cancer, breast cancer, dermatofibroma, mesothelioma and melanoma.

Reagents and Equipment

Antigen retrieval was performed using Reveal (RV) (pH 6.0) and BORG Decloaker (BD) (pH, 9.5) in a Decloaking Chamber (pressure cooker) for 30 seconds at 125° C. and 20 p.s.i. (BIOCARE Medical). For microarray tissues, antigen retrieval was performed overnight at 75° C. and placed in RV or Nuclear Decloaker (pH 9.5) (BIOCARE Medical). Antibody cocktails are listed in Table 1. All antibodies were diluted for optimum titer, followed by biotin-free polymer detection kits and reagents (Table 2). TBS wash buffer was used on the following automated stainers: AutoStainer (Dako), i6000 BioGenex, Nemesis (BIOCARE Medical).

TABLE 1

| Antibody Cocktail | Host | Clone |
|---|---|---|
| ApoptoticCK18 | Mouse | BC/M30 |
| Ki-67 | Rabbit | SP91 |
| CD34 | Mouse | Biocare |
| Factor XIIIa | Rabbit | Polyclonal |
| L26 | Mouse | L26 |
| CD3 | Rabbit | Polyclonal |
| Kappa | Mouse | KDB-1 |
| Lambda | Rabbit | Polyclonal |
| CK5 | Mouse | XM26 |
| P63 | Mouse | BC4A4 |
| CK8/18 | Mouse | 5D3 |
| CK5 | Mouse | XM26 |
| CK17 | Mouse | $K_S$17.E3 |
| CK8/18 | Mouse | 5D3 |
| HMW CK | Mouse | DE-SQ |
| p63 | Mouse | BC4A4 |
| P504S | Rabbit | P504S |
| MART-1 | Mouse | M2-7C10 + M2-9E3 |
| Tyrosinase | Mouse | T311 |
| S100 | Rabbit | Polyclonal |
| Ki-67 | Mouse | DVB-1 |
| Caspase-3 | Rabbit | Polyclonal |
| CK5/6 | Mouse | CK5/6.007 |
| Calretinin | Rabbit | SP19 |
| CD10 | Mouse | 56C6 (HSA) |
| PSA | Rabbit | Polyclonal |
| HSA | Mouse | OCH1E5 |

Antibody cocktails were obtained from Biocare Medical

TABLE 2

| Name | Kit or secondary reagents |
|---|---|
| Double Stain Detection Kit #1 | Goat anti-mouse alkaline phosphatase (AP) |
| | Goat anti-rabbit horseradish peroxidase (HRP) |
| Double Stain Detection Kit #2 | Goat anti-mouse HRP |
| | Goat anti-rabbit AP |
| MACH 2 ™ Mouse-HRP | Goat anti-mouse (HRP) |
| MACH 2 ™ Mouse-AP | Goat anti-mouse (AP) |
| MACH 2 ™ Rabbit-HRP | Goat anti-rabbit (HRP) |
| MACH 2 ™ Rabbit-AP | Goat anti-rabbit (AP) |

Double stains kits, reagents and chromogens were obtained from Biocare Medical

TABLE 3

| Antibody Cocktail | Pretreatment | Detection | Chromogens |
|---|---|---|---|
| Apoptotic/CK18 + Ki-67 | BORG Decloaker ™ | DS Kit #1 | DAB and Fast Red |
| CD34 + Factor XIIIa | Trypsin | DS Kit #2 | DAB and Fast Red |
| L26 + CD3 | Reveal | DS Kit #1 | DAB and Fast Red |
| Kappa + Lambda | Reveal | DS Kit #2 | DAB and Fast Red |
| CK5 + CK17 + CK8/18 | Reveal | DS Kit #2 | DAB and Fast Red |
| CK5 + p63 + CK8/18 | Reveal | DS kit #2 + MACH 2-HRP | DAB and Fast Red |
| HMW CK + p63 + P504S | BORG Decloaker | DS Kit #2 | DAB and Fast Red |
| MART-1 + Tyrosinase + S100 | Reveal | DS Kit #2 | DAB and Fast Red |
| Ki-67 + Caspase-3 | BORG Decloaker | DS Kit #2 | DAB and Fast Red |
| CK5/6 + Calretinin | Reveal | DS Kit #2 | DAB and Fast Red |
| CD10 + PSA + HSA | Reveal | DS Kit #2 + M2 Mouse-HRP | B. Purple and Fast Red DAB |
| LCA + S100 + CK8/18 | Reveal | DS Kit #2 + M2 Rabbit-HRP | DAB and Fast Red Bajoran Purple |

*Double stains kits, reagents, antibodies, and chromogens were obtained from Biocare Medical All of the above reagents were tested on tissues mounted on slides and exhibited good double and triple staining patterns.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of detecting presence and/or distribution of three antigens in a sample, comprising:
    simultaneously contacting a sample with a primary antibody cocktail comprising a buffer aqueous solution of anti-P504S antibody from a first animal species as a first primary antibody, anti-p63 antibody from a second animal species different from the first animal species as a second primary antibody, and anti-high molecular weight cytokeratin (anti-HMWCK) antibody from the second animal species as a third primary antibody, wherein the sample is a tissue or cell, under conditions sufficient for the primary antibodies to specifically bind to antigens in the sample;
    simultaneously contacting the sample, which has been previously simultaneously contacted with the primary antibody cocktail with a composition comprising a first secondary antibody and a second secondary antibody under conditions sufficient to form secondary antibody complexes with the primary antibodies to antigens in the contacted sample,
    wherein the first secondary antibody is specific for the anti-P504S primary antibody in the primary antibody cocktail and the second secondary antibody is specific for the rest of the primary antibodies in the primary antibody cocktail,
    wherein the first secondary antibody is coupled to a poly (alkaline phosphatase) (poly AP) moiety and the second secondary antibody is coupled to a poly (horseradish peroxidase) (poly HRP) moiety, and
    wherein the composition comprises a buffer for the first and second secondary antibodies; and
    applying two different chromogens that result in two different colors for separately detecting the bound poly HRP moiety and the bound poly AP moiety on the secondary antibody-contained sample, thereby detecting the secondary antibody complexes on the contacted sample as indicative of the presence and/or distribution of the P504S, p63, and/or HMWCK antigens in the sample,
    wherein the two different chromogens are (i) 3,3'-diaminobenzidine (DAB) for detecting the poly HRP moiety and (ii) a combination of at least one Fast Red salt with at least one naphthol phosphate (Fast Red) for detecting the poly AP moiety.

2. The method of claim 1, wherein the sample is contained in an automated staining device and wherein the contacting occurs in the automated staining device.

3. The method of claim 1, wherein the first primary antibody is a rabbit monoclonal or polyclonal antibody.

4. The method of claim 1, wherein the primary antibodies other than the first primary antibody are mouse antibodies.

5. The method of claim 4, wherein the first secondary antibody is a goat anti-rabbit antibody and the second secondary antibody is a goat anti-mouse antibody.

6. The method of claim 1, wherein the method is completed in not more than 15 steps including washing steps.

7. The method of claim 1, wherein the buffered aqueous solution of the primary antibody cocktail comprises 2-methyl-4-isothiazolin-3-one as a preservative.

8. The method of claim 1, wherein the method is completed in 2 to 2.5 hour.

9. The method of claim 1, wherein the primary antibody cocktail consists of anti-P504S antibody, anti-p63 antibody, and anti-HMWCK antibody.

10. A detecting system for detecting antigens in a sample comprising at least four separately contained reagents:
    the first separately contained reagent being a primary antibody cocktail comprising a buffer aqueous solution of anti-P504S antibody from a first animal species as a first primary antibody, anti-p63 antibody from a second animal species different from the first animal species as a second primary antibody, and anti-high molecular weight cytokeratin (anti-HMWCK) antibody from the second animal species as a third primary antibody;
    the second separately contained reagent being a buffer composition comprising a first secondary antibody and a second secondary antibody,
    wherein the first secondary antibody is specific for the anti-P504S primary antibody antibodies in the primary antibody cocktail and the second secondary antibody is specific for the rest of the primary antibodies in the primary antibody cocktail, and
    wherein the first secondary antibody is coupled to a poly (alkaline phosphatase) (poly AP) moiety and the a second secondary antibody is coupled to a poly (horseradish peroxidase) (poly HRP) moiety; and
    at least two different separately contained chromogen reagents that result in at least two different colors,
    wherein a first separately contained chromogen reagent is for detecting the poly HRP moiety and is selected from the group consisting of 3,3'-diaminobenzidine (DAB), 3-amino-9-ethylcarbazole (AEC), and 4-chloro-l-naphthol (Bajoran Purple), and
    wherein a second separately contained chromogen reagent is for detecting the poly AP moiety and is a combination of at least one Fast Red salt with at least one naphthol phosphate (Fast Red), and a combination of at least one Fast Blue salt with at least one naphthol phosphate (Fast or Ferangi Blue).

11. The composition of claim 10, wherein the primary antibody cocktail consists of anti-P504S antibody, anti-p63 antibody, and anti-HMWCK antibody.

12. The detecting system of claim 10, wherein the primary antibodies other than the first primary antibody are mouse antibodies.

13. The detecting system of claim 12, wherein the first secondary antibody is a goat anti-rabbit antibody and the second secondary antibody is a goat anti-mouse antibody.

* * * * *